United States Patent [19]

Wissner et al.

[11] Patent Number: 5,569,762
[45] Date of Patent: Oct. 29, 1996

[54] ASYMMETRIC SYNTHESIS OF INTERMEDIATES FOR RETROVIRAL PROTEASE INHIBITOR COMPOUNDS

[75] Inventors: Allan Wissner, Ardsley; Michael P. Trova, Salisbury Mills, both of N.Y.

[73] Assignee: American Cyanamid Company, Madison, N.J.

[21] Appl. No.: 408,362

[22] Filed: Mar. 22, 1995

Related U.S. Application Data

[62] Division of Ser. No. 181,924, Jan. 14, 1994, Pat. No. 5,428,167.

[51] Int. Cl.⁶ .................................................. C07D 217/00
[52] U.S. Cl. ........................................... 546/146; 546/147
[58] Field of Search ................................. 546/146, 147

[56] References Cited

U.S. PATENT DOCUMENTS

| | | | |
|---|---|---|---|
| 5,142,056 | 8/1992 | Kempe | 546/265 |
| 5,169,952 | 12/1992 | Askin . | |
| 5,188,950 | 2/1993 | Balani | 435/120 |
| 5,192,668 | 3/1993 | Treiber | 435/41 |
| 5,254,697 | 10/1993 | Waterson | 549/313 |

FOREIGN PATENT DOCUMENTS

| | | | |
|---|---|---|---|
| 402646 | 12/1990 | European Pat. Off. | 435/41 |
| 541168 | 12/1993 | European Pat. Off. | 435/41 |
| 9309096 | 5/1993 | WIPO | 432/41 |

OTHER PUBLICATIONS

Donati et al, *Aust. J. Chem.*, vol. 43, 1990, pp. 375–381.
Sandstrom et al, Drugs, vol. 34, pp. 373–390, 1987.
Bradbury, et al., Tetrahedren Letters, vol. 30 pp. 3845–3848, 1989.
Herold, et al., J. Org. Chem., 1989, 54, 1178–1185.
Thompson, et al., J. Med. Chem., 1992, 35, 1685–1701.
Young, et al., J. Med. Chem., 1992, 35, 1702–1709.
Rich, et al., J. Med. Chem., 1991, 34, 1225–1228.
Ghosh, et al., J. Org. Chem., 1993, 58, 1025–1029.
Ghosh, et al., J. Org. Chem., 1991, 56, 6500–6503.
Evan, et al., J. Org. Chem., 1985, 50, 4615–4625.
Fray, et al., J. Org. Chem., 1986, 51, 4828–4833.

*Primary Examiner*—Zinna Northington Davis
*Attorney, Agent, or Firm*—Thomas S. Szatkowski; R. F. Boswell, Jr.

[57] ABSTRACT

The disclosure describes an improved process for producing optically active compounds of Formula II or III, which compounds are useful as intermediates for preparing compounds active as inhibitors of retroviral protease enzymes:

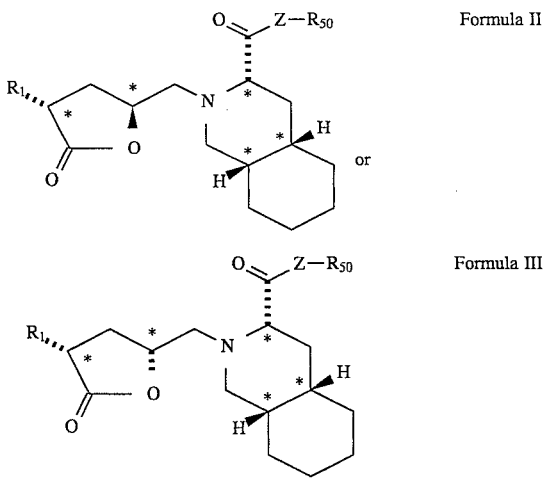

wherein $R_1$, $R_{50}$ and Z are described in the specification. The improved process includes either synthesis of diastereomeric iodolactones which are separated prior to conversion to compounds of Formula II or III or synthesis of an epoxide which is converted directly to compounds of Formula II and III.

2 Claims, No Drawings

5,569,762

ASYMMETRIC SYNTHESIS OF INTERMEDIATES FOR RETROVIRAL PROTEASE INHIBITOR COMPOUNDS

This is a divisional of application Ser. No. 08/181,924 filed on Jan. 14, 1994, now U.S. Pat. No. 5,428,167.

BACKGROUND OF THE INVENTION

1. Field of the Invention

The invention relates to an improved process for producing optically active compounds which are useful as intermediates for compounds which are inhibitors of retroviral protease enzymes and anti-HIV agents and to certain novel intermediate compounds utilized in the novel process.

SUMMARY OF THE INVENTION

It will be appreciated that those skilled in the art recognize that the atoms labelled with an asterisk (*) represent an optically active asymmetric center.

The invention provides an improved process for producing optically active compounds of Formula II or III, which compounds are useful as intermediates for preparing compounds active as inhibitors of retroviral protease enzymes:

Formula II

Formula III wherein:

$R_{50}$ is a straight or branched $(C_1-C_7)$alkyl;

Z is a single bond, oxygen or NH;

$R_1$ is hydrogen; straight or branched $(C_1-C_7)$alkyl;
—$(CH_2)_n$-cyclic$(C_3-C_7)$alkyl, n=0–4; —$(CH_2)_n$-phenyl, n=0–4; or —$(CH_2)_n$-substituted phenyl, n=0–4, and substituted with F, Cl, Br, I, $(C_1-C_4)$alkoxide, straight, branched or cyclic $(C_1-C_6)$alkyl or phenyl.

An improved process according to the present invention to produce an optically active compound according to Formula II comprises:

a) deprotonating a compound of the formula:

wherein $R_1$ is hydrogen; straight or branched $(C_1-C_7)$alkyl;
—$(CH_2)_n$-cyclic$(C_3-C_7)$alkyl, n=0–4; —$(CH_2)_n$-phenyl, n=0–4; or —$(CH_2)_n$-substituted phenyl, n=0–4, and substituted with F, Cl, Br, I, $(C_1-C_4)$alkoxide, straight, branched or cyclic $(C_1-C_6)$alkyl or phenyl;

D is $(C_1-C_7)$alkyl or —$(CH_2)_n$-phenyl, n=0–4; and

E and G are the same or different and are hydrogen, $(C_1-C_7)$alkyl or —$(CH_2)_n$-phenyl, n=0–4; and then alkylating with allyl iodide to obtain a compound of the formula:

wherein $R_1$, D, E, and G are as defined hereinabove;

b) hydrolyzing the compound obtained from step a to remove the oxazolidinone portion and obtain a compound of the formula:

wherein $R_1$ is as defined hereinabove;

c) reacting the compound obtained from step b with dimethylamine to obtain a compound of the formula:

wherein $R_1$ is as defined hereinabove:

d) subjecting the compound obtained from step c to iodolactonization conditions to obtain a mixture of diastereomers, 3R-cis, 3R-trans, of the formula:

Isomer A (trans)    Isomer B (cis)

wherein $R_1$ is as defined hereinabove; and separating the isomers to obtain a purified trans-iodolactone (Isomer A); and e) coupling the purified trans-iodolactone obtained from step d (Isomer A) with a compound of formula:

via iodide displacement wherein $R_{50}$ is a straight or branched $(C_1-C_7)$alkyl and Z is a single bond, oxygen or NH; to obtain a compound of the formula:

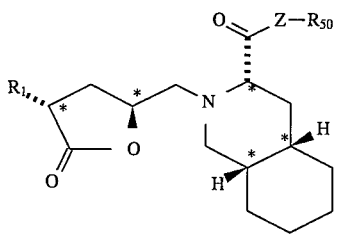

Formula II wherein $R_1$, $R_{50}$ and $Z$ are as defined hereinabove.

An improved process according to the present invention to produce an optically active compound according to Formula III, comprises:

a) deprotonating a compound of the formula:

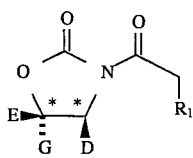

wherein $R_1$ is hydrogen; straight or branched $(C_1-C_7)$alkyl; $-(CH_2)_n$-cyclic$(C_3-C_7)$alkyl, n=0–4; $-(CH_2)_n$-phenyl, n=0–4; or $-(CH_2)_n$-substituted phenyl, n=0–4, and substituted with F, Cl, Br, I, $(C_1-C_4)$ alkoxide, straight, branched or cyclic $(C_1-C_6)$alkyl or phenyl;

D is $(C_1-C_7)$alkyl or $-(CH_2)_n$-phenyl, n=0–4; and

E and G are the same or different and are hydrogen, $(C_1-C_7)$alkyl or $-(CH_2)_n$-phenyl, n=0–4; and then alkylating with allyl iodide to obtain a compound of the formula:

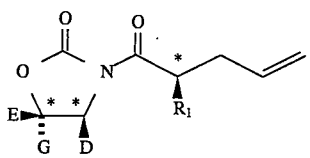

wherein $R_1$, D, E, and G are as defined hereinabove;

b) hydrolyzing the compound obtained from step a to remove the oxazolidinone portion and obtain a compound of the formula:

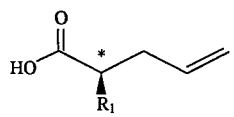

wherein $R_1$ is as defined hereinabove;

c) subjecting the compound obtained from step b to iodolactonization conditions to obtain a mixture of diastereomers, 3R-cis, 3R-trans, of the formula:

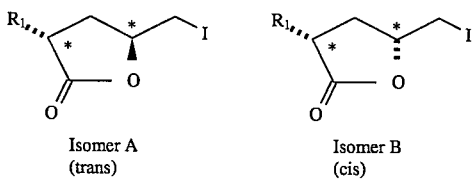

Isomer A (trans)   Isomer B (cis)

wherein $R_1$ is as defined hereinabove; and separating the isomers to obtain a purified cis-iodolactone (isomer B);

d) coupling the purified cis-iodolactone obtained from step c (Isomer B) with a compound of formula:

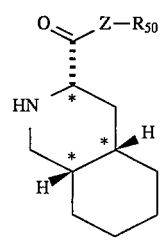

via iodide displacement wherein $R_{50}$ is a straight or branched $(C_1-C_7)$alkyl and Z is a single bond, oxygen or NH; to obtain a compound of the formula:

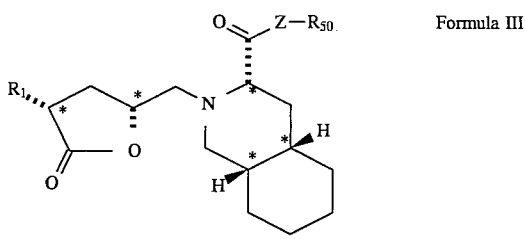

Formula III wherein $R_1$, $R_{50}$ and Z are as defined hereinabove.

An alternative improved process to obtain a compound of the formula II or III comprises:

a) deprotonating a compound of the formula:

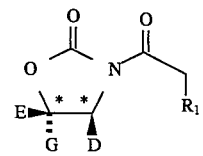

wherein $R_1$ is hydrogen; straight or branched $(C_1-C_7)$alkyl; $-(CH_2)_n$-cyclic$(C_3-C_7)$alkyl, n=0–4; $-(CH_2)_n$-phenyl, n=0–4; or $-(CH_2)_n$-substituted phenyl, n=0–4, and substituted with F, Cl, Br, I, $(C_1-C_4)$alkoxide, straight, branched or cyclic $(C_1-C_6)$alkyl or phenyl;

D is $(C_1-C_7)$alkyl or $-(CH_2)_n$-phenyl, n=0–4; and

E and G are the same or different and are hydrogen, $(C_1-C_7)$alkyl or $-(CH_2)_n$-phenyl, n=0–4; and then alkylating with allyl iodide to obtain a compound of the formula:

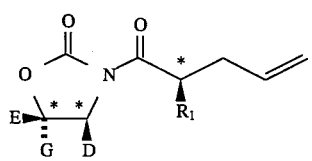

wherein $R_1$, D, E, G are as defined hereinabove;

b) epoxidizing the compound obtained from step a to obtain a compound of the formula:

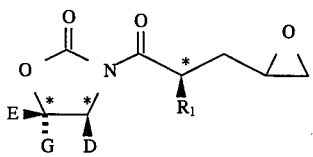

wherein $R_1$, D, E, and G are as defined hereinabove;

c) coupling the compound obtained from step b with a compound of the formula:

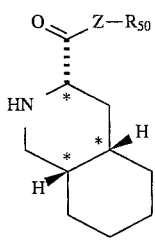

via displacement of the epoxide and concomitant lactonization wherein $R_{50}$ is a straight or branched $(C_1-C_7)$alkyl and Z is a single bond, oxygen or NH; to obtain a diastereomeric mixture of compounds of the formulae:

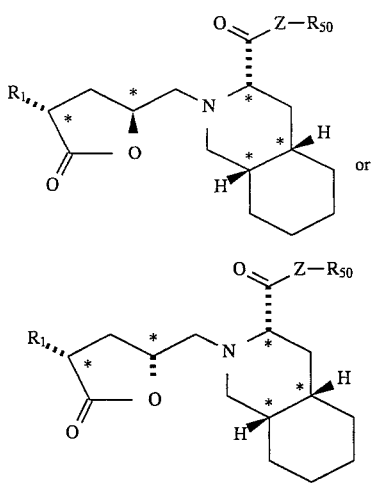

wherein $R_1$, $R_{50}$ and Z are as defined hereinabove;

d) separating the diastereomeric mixture obtained from step c to obtain a purified compound of Formula II or a purified compound of Formula III.

The invention also provides an improved process for converting the intermediate compounds of Formula II or Formula III into the optically active retroviral protease inhibitor compounds of formula Ia and Ib:

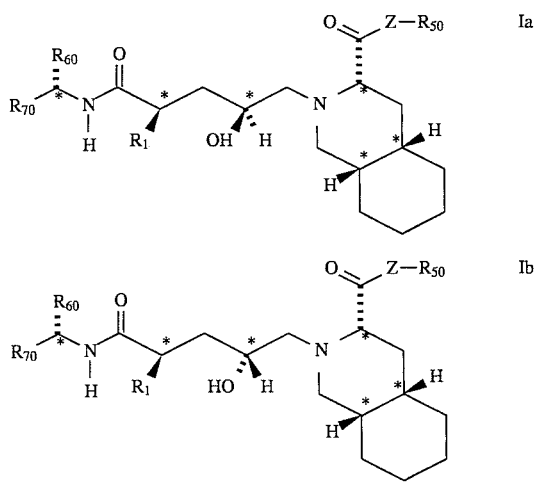

wherein:

$R_{50}$ is a straight or branched $(C_1-C_7)$alkyl;

Z is a single bond, oxygen or NH;

$R_1$ is hydrogen; straight or branched $(C_1-C_7)$alkyl; —$(CH_2)_n$-cyclic$(C_3-C_7)$alkyl, n=0–4; —$(CH_2)_n$-phenyl, n=0–4; or —$(CH_2)_n$-substituted phenyl, n=0–4, and substituted with F, Cl, Br, I, $(C_1-C_4)$alkoxide, straight, branched or cyclic $(C_1-C_6)$alkyl or phenyl;

$R_{60}$ is a straight or branched $(C_1-C_7)$alkyl;

—$(CH_2)_n$-cyclic $(C_3-C_7)$alkyl, n=0–4; —$(CH_2)_2CONH_2$; —$CH_2CONH_2$; —$CH_2OH$ or —$CH(CH_3)OH$;

$R_{70}$ is a moiety of the formula:

wherein $W_1$ is —$NH(CH_2)_j$-phenyl, j=0–1;

—$NH(CH_2)_j$-substituted phenyl, j=0–1, substituted with F, Cl, Br, I, $(C_1-C_4)$alkoxide, straight, branched or cyclic $(C_1-C_6)$alkyl; —$NH(CH_2)_j$-T, j=0–1, wherein T is selected from piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoazolidinyl, morpholinyl, thiazolyl, thiazolidinyl, isothiazolyl, benzofuranyl, benzodioxanonyl, quinuclidinyl, isothiazolidinyl, indolyl, quinolinyl, isoquinolinyl, benzimidazolyl, thiadiazoyl, benzopyranyl, benzothiapyranyl, benzothiazolyl, benzoxaolyl, furyl, tetrahydrofuryl, tetrahydropyranyl, thienyl, benzothienyl, thiamorpholinyl, thiamorpholinyl sulfoxide, thiamorpholinyl sulfone and oxadiazolyl; or —$NH(CH_2)_j$-substituted T, j=0–1, T is as defined hereinabove, substituted with F, Cl, I, Br, $(C_1-C_4)$alkoxide, or straight, branched or cyclic $(C_1-C_6)$alkyl.

The improved process to produce Ib, comprises:

a) hydrolyzing a compound of Formula III to obtain a compound of the formula:

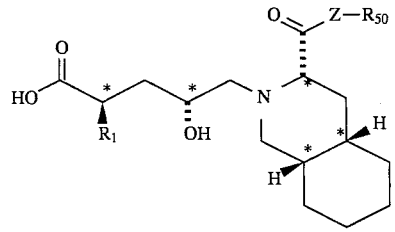

wherein $R_1$, $R_{50}$ and Z are as defined hereinabove;

b) protecting the alcohol and carboxylic acid functionalities of the compound obtained from step a to obtain a compound of the formula:

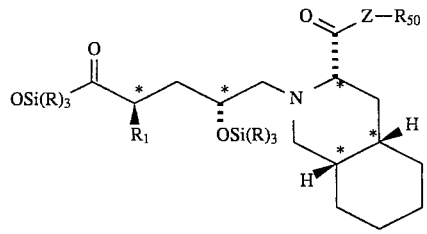

wherein $R_1$, $R_{50}$ and Z are as defined hereinabove and R is a straight or branched $(C_1-C_6)$alkyl or phenyl;

c) selectively deprotecting the carboxylic acid functionality of the compound obtained from step b to obtain a compound of the formula:

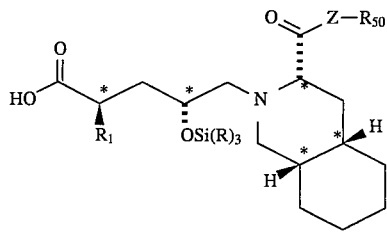

wherein R, $R_1$, $R_{50}$ and Z are as defined hereinabove;

d) reacting the deprotected carboxylic acid functionality of the compound obtained from step c with a compound of the formula:

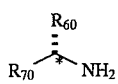

wherein $R_{60}$ is a straight or branched $(C_1-C_7)$alkyl; —$(CH_2)_n$-cyclic $(C_3-C_7)$alkyl, n=0–4; —$(CH_2)_2CONH_2$; —$CH_2CONH_2$; —$CH_2OH$ or —$CH(CH_3)OH$;

$R_{70}$ is a moiety of the formula:

wherein $W_1$ is —$NH(CH_2)_j$-phenyl, j=0–1;

—$NH(CH_2)_j$-substituted phenyl, j=0–1, substituted with F, Cl, Br, I, $(C_1-C_4)$alkoxide, straight, branched or cyclic $(C_1-C_6)$alkyl; —$NH(CH_2)_j$-T, j=0–1, wherein T is selected from piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoazolidinyl, morpholinyl, thiazolyl, thiazolidinyl, isothiazolyl, benzofuranyl, benzodioxanonyl, quinuclidinyl, isothiazolidinyl, indolyl, quinolinyl, isoquinolinyl, benzimidazolyl, thiadiazoyl, benzopyranyl, benzothiapyranyl, benzothiazolyl, benzoxaolyl, furyl, tetrahydrofuryl, tetrahydropyranyl, thienyl, benzothienyl, thiamorpholinyl, thiamorpholinyl sulfoxide, thiamorpholinyl sulfone and oxadiazolyl; or —$NH(CH_2)_j$-substituted T, j=0–1, T is as defined hereinabove, substituted with F, Cl, I, Br, $(C_1-C_4)$alkoxide, or straight, branched or cyclic $(C_1-C_6)$alkyl; to obtain a compound of the formula:

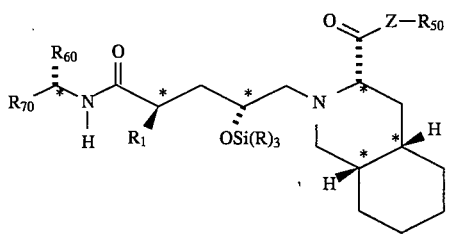

wherein R, $R_1$, $R_{50}$, $R_{60}$, $R_{70}$ and Z are as defined hereinabove; and i) deprotecting the alcohol functionality of the compound obtained from step d to obtain the compound of formula Ib.

The improved process to produce Ia, comprises:

a) hydrolyzing a compound of Formula II to obtain a compound of the formula:

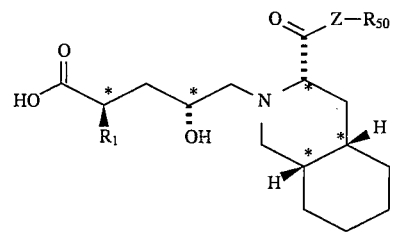

wherein $R_1$, $R_{50}$ and Z are as defined hereinabove;

b) protecting the alcohol and carboxylic acid functionalities of the compound obtained from step a to obtain a compound of the formula:

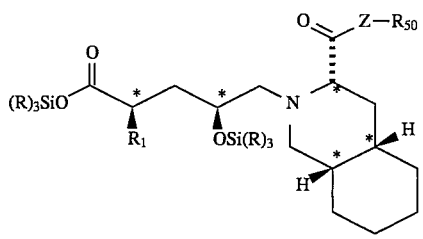

wherein $R_1$, $R_{50}$ and Z are as defined hereinabove and R is a straight or branched $(C_1-C_6)$alkyl or phenyl;

c) selectively deprotecting the carboxylic acid functionality of the compound obtained from step b to obtain a compound of the formula:

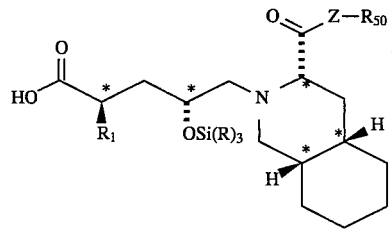

wherein R, $R_1$, $R_{50}$ and Z are as defined hereinabove;

d) reacting the deprotected carboxylic acid functionality of the compound obtained from step c with a compound of the formula:

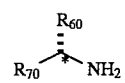

wherein $R_{60}$ is a straight or branched $(C_1-C_7)$alkyl; —$(CH_2)_n$-cyclic $(C_3-C_7)$alkyl, n=0–4; —$(CH_2)_2CONH_2$; —$CH_2CONH_2$; —$CH_2OH$ or —$CH(CH_3)OH$;

$R_{70}$ is a moiety of the formula:

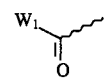

wherein $W_1$ is —$NH(CH_2)_j$-phenyl, j=0–1;

—$NH(CH_2)_j$-substituted phenyl, j=0–1, substituted with F, Cl, Br, I, $(C_1-C_4)$alkoxide, straight, branched or cyclic $(C_1-C_6)$alkyl;

—NH(CH$_2$)$_j$-T, j=0–1, wherein T is selected from piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoazolidinyl, morpholinyl, thiazolyl, thiazolidinyl, isothiazolyl, benzofuranyl, benzodioxanonyl, quinuclidinyl, isothiazolidinyl, indolyl, quinolinyl, isoquinolinyl, benzimidazolyl, thiadiazoyl, benzopyranyl, benzothiapyranyl, benzothiazolyl, benzoxaolyl, furyl, tetrahydrofuryl, tetrahydropyranyl, thienyl, benzothienyl, thiamorpholinyl, thiamorpholinyl sulfoxide, thiamorpholinyl sulfone and oxadiazolyl; or —NH(CH$_2$)$_j$-substituted T, j=0–1, T is as defined hereinabove, substituted with F, Cl, I, Br, (C$_1$–C$_4$)alkoxide, or straight, branched or cyclic (C$_1$–C$_6$)alkyl; to obtain a compound of the formula:

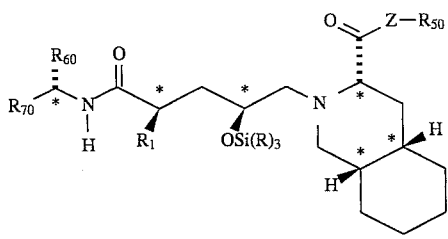

wherein R, R$_1$, R$_{50}$, R$_{60}$, R$_{70}$ and Z are as defined hereinabove; and e) deprotecting the alcohol functionality of the compound obtained from step d to obtain the compound of formula Ia.

Also included in the present invention are certain novel intermediate compounds useful as intermediates for producing the retroviral protease inhibitor compounds of Formula Ia or Ib. Such intermediate compounds include those of the formula:

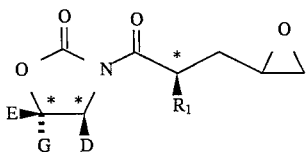

wherein

R$_1$ is hydrogen; straight or branched (C$_1$–C$_7$) alkyl;

—(CH$_2$)$_n$-cyclic(C$_3$–C$_7$)alkyl, n=0–4;

—(CH$_2$)$_n$-phenyl, n=0–4; or

—(CH$_2$)$_n$-substituted phenyl, n=0–4, and substituted with F, Cl, Br, I, (C$_1$–C$_4$)alkoxide, straight, branched or cyclic (C$_1$–C$_6$)alkyl or phenyl;

D is (C$_1$–C$_7$)alkyl or —(CH$_2$)$_n$-phenyl, n=0–4;

E and G are the same or different and are hydrogen, (C$_1$–C$_7$)alkyl or —(CH$_2$)$_n$-phenyl, n=0–4.

Additional novel intermediates according to the present invention useful for producing the retroviral protease inhibitor compounds of Formula Ia or Ib include those of the formulae:

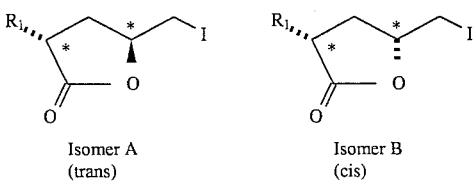

Isomer A (trans)   Isomer B (cis)

wherein

R$_1$ is hydrogen; straight or branched (C$_1$–C$_7$)alkyl;

—(CH$_2$)$_n$-cyclic(C$_3$–C$_7$)alkyl, n=0–4;

—(CH$_2$)$_n$-phenyl, n=0–4; or

—(CH$_2$)$_n$-substituted phenyl, n=0–4, and substituted with F, Cl, Br, I, (C$_1$–C$_4$)alkoxide, straight, branched or cyclic (C$_1$–C$_6$)alkyl or phenyl.

DESCRIPTION OF THE PREFERRED EMBODIMENTS

The novel process of the present invention will be described in greater detail with reference to the following schemes:

Scheme 1

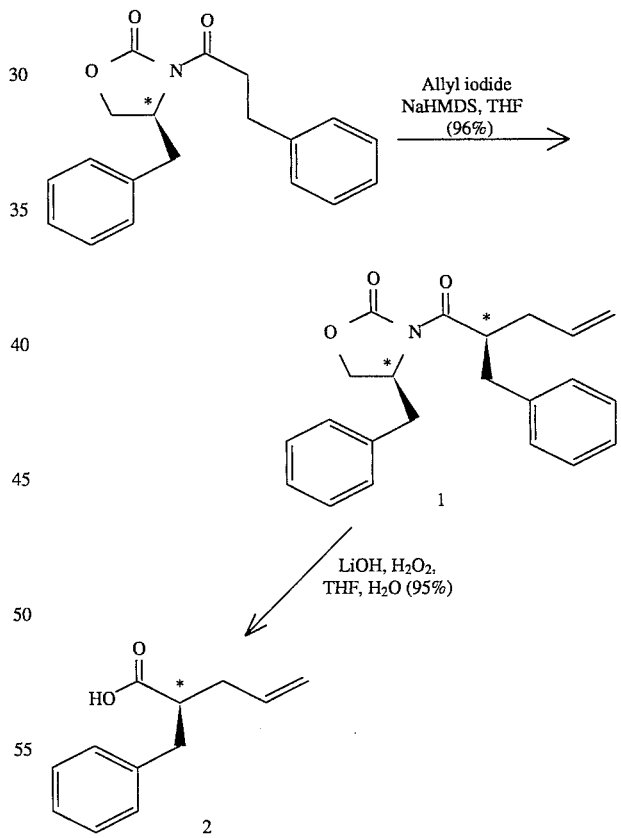

Scheme 2
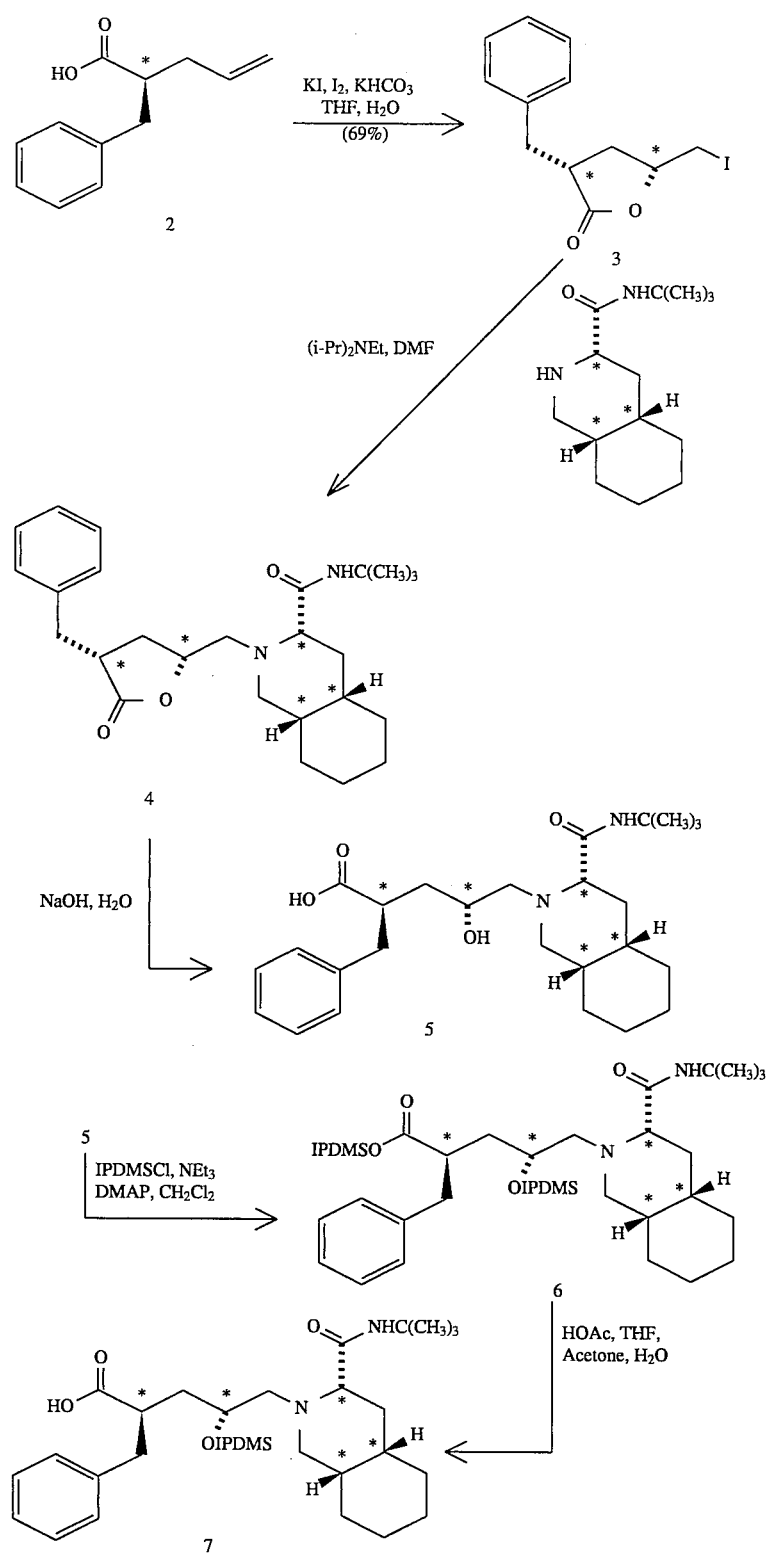

-continued
Scheme 2
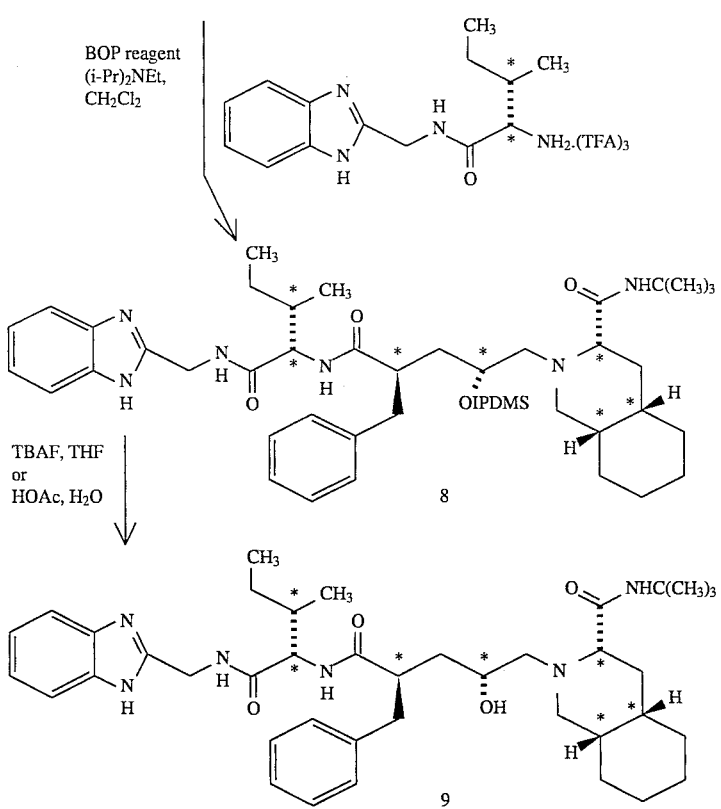
Scheme 3
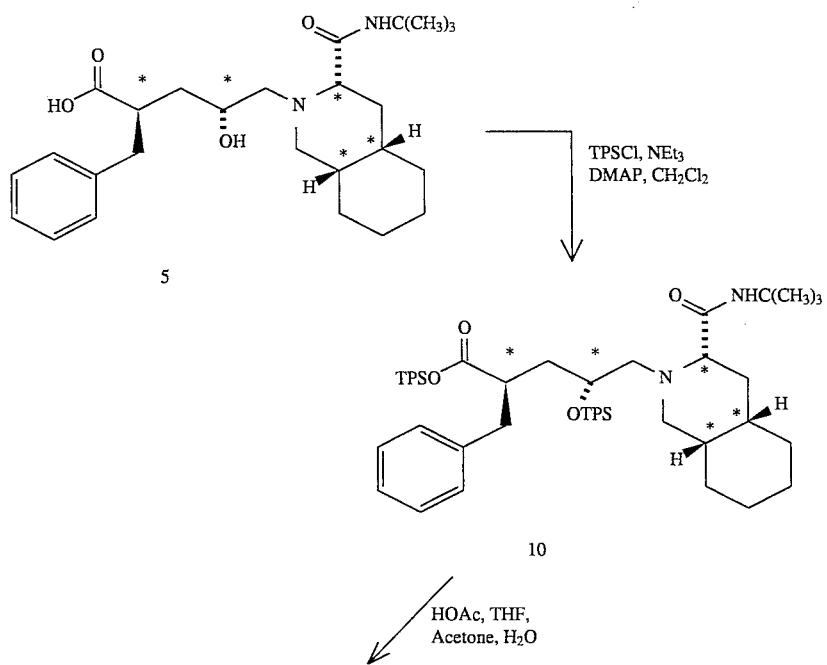

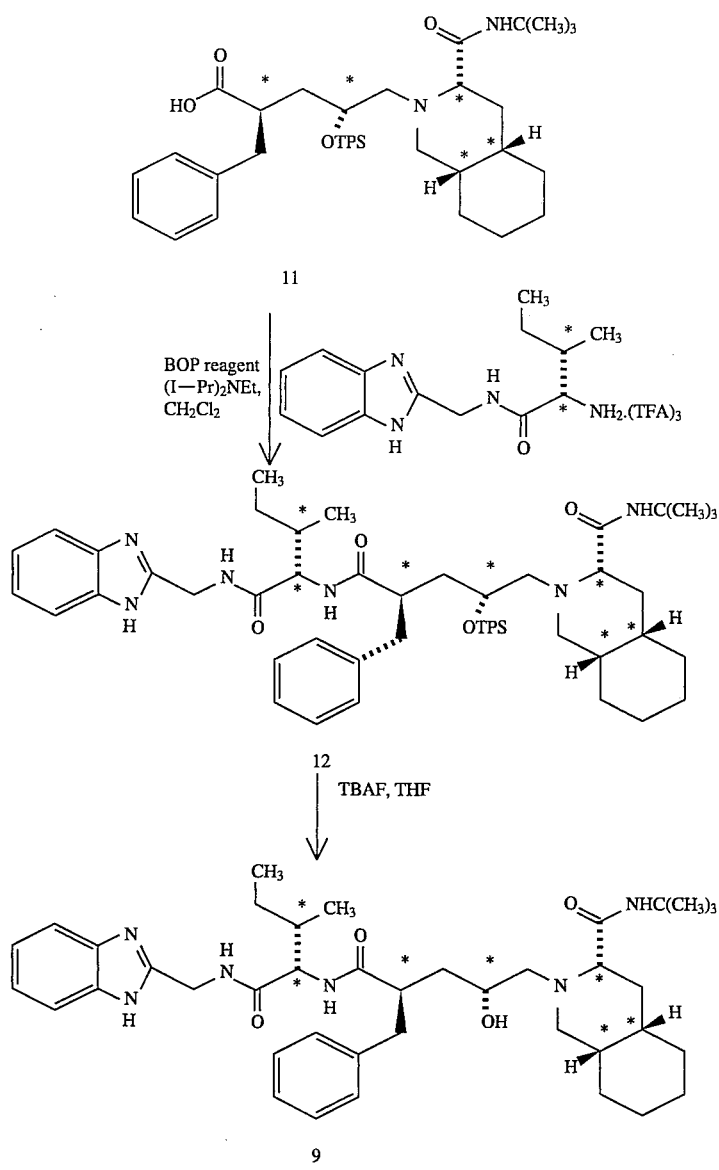
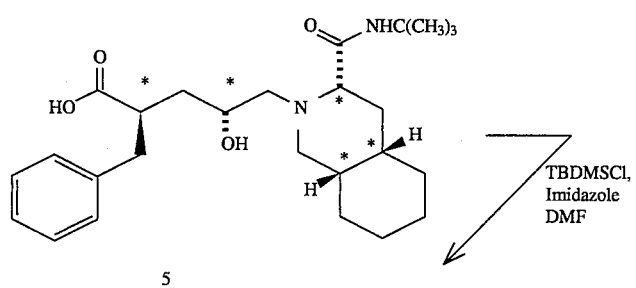

5,569,762
17
-continued
Scheme 4
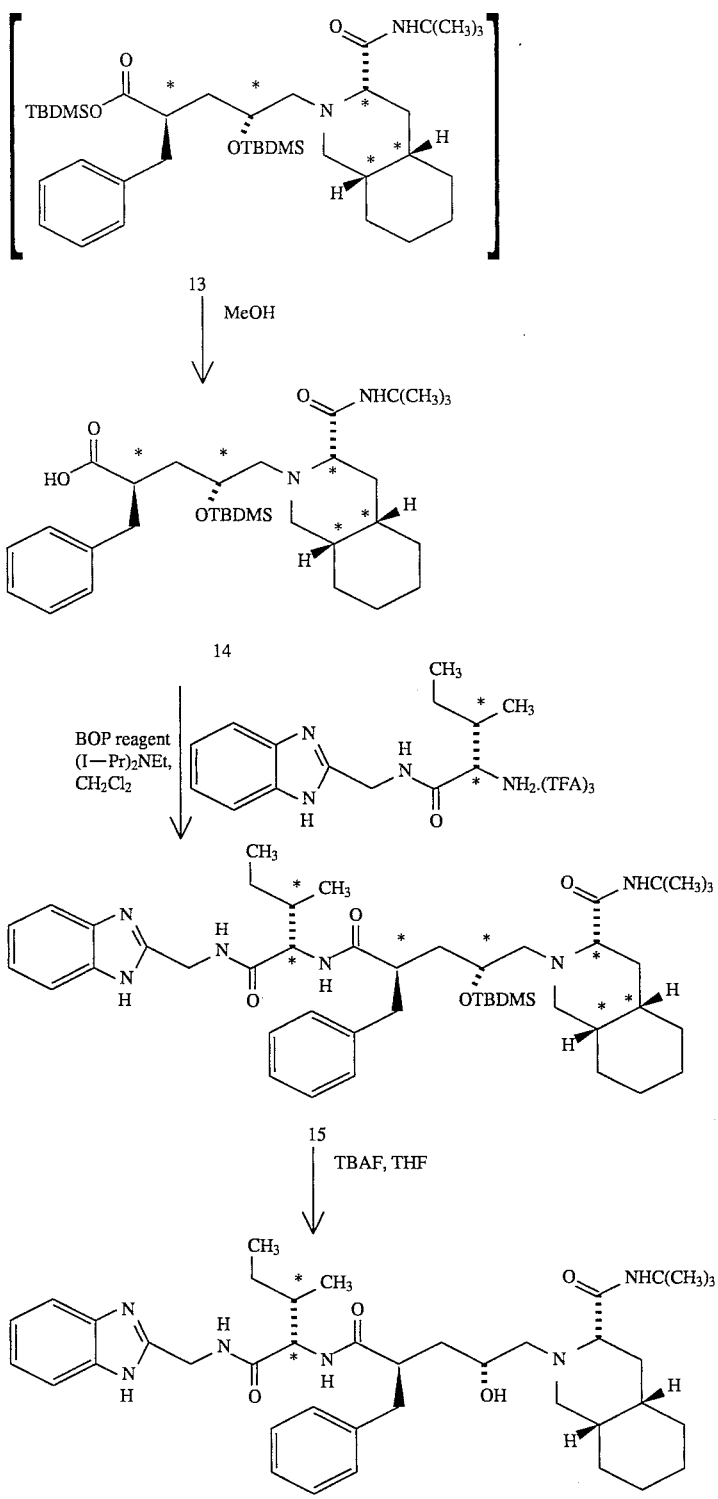

Scheme 5
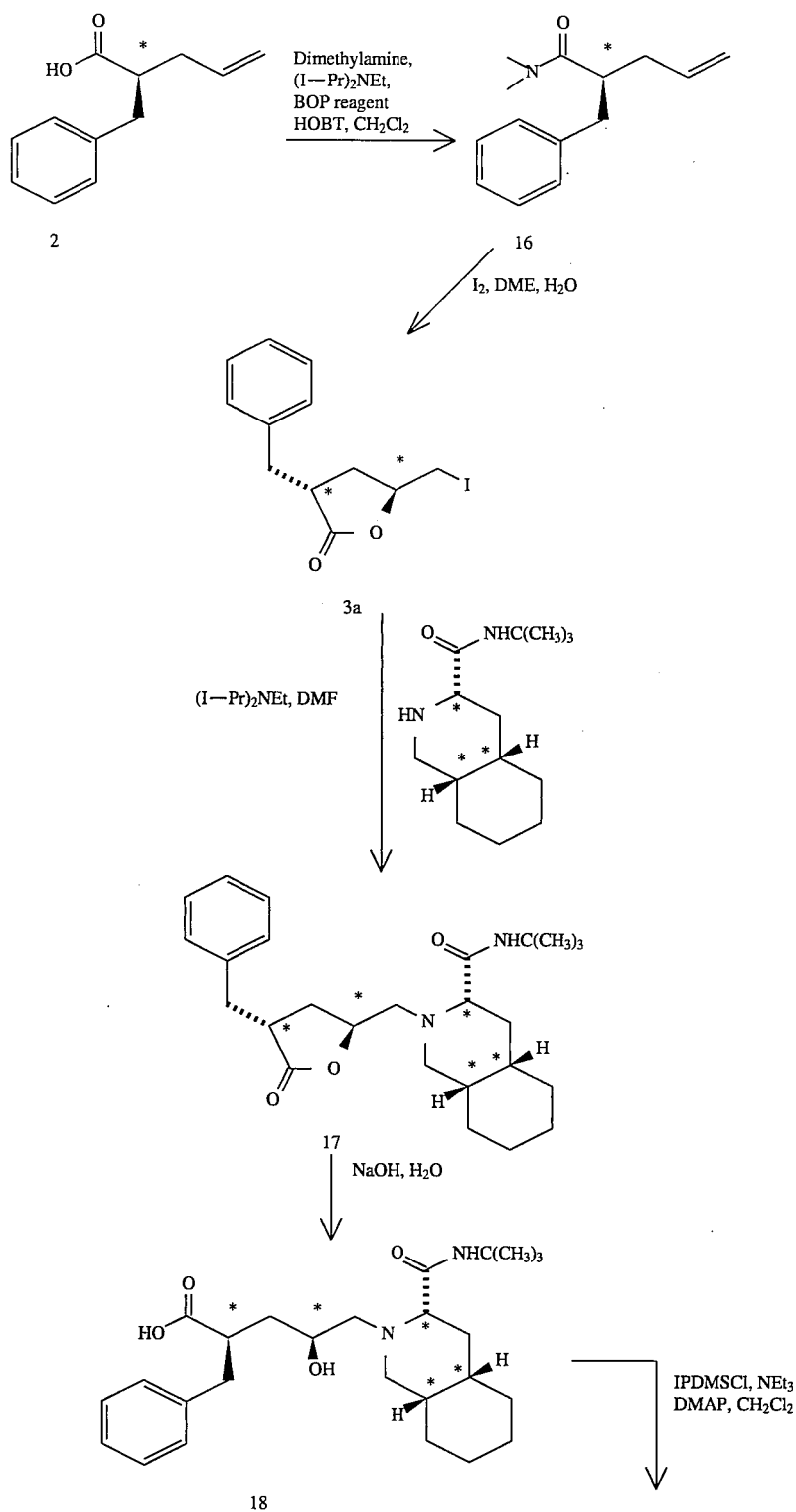

-continued
Scheme 5
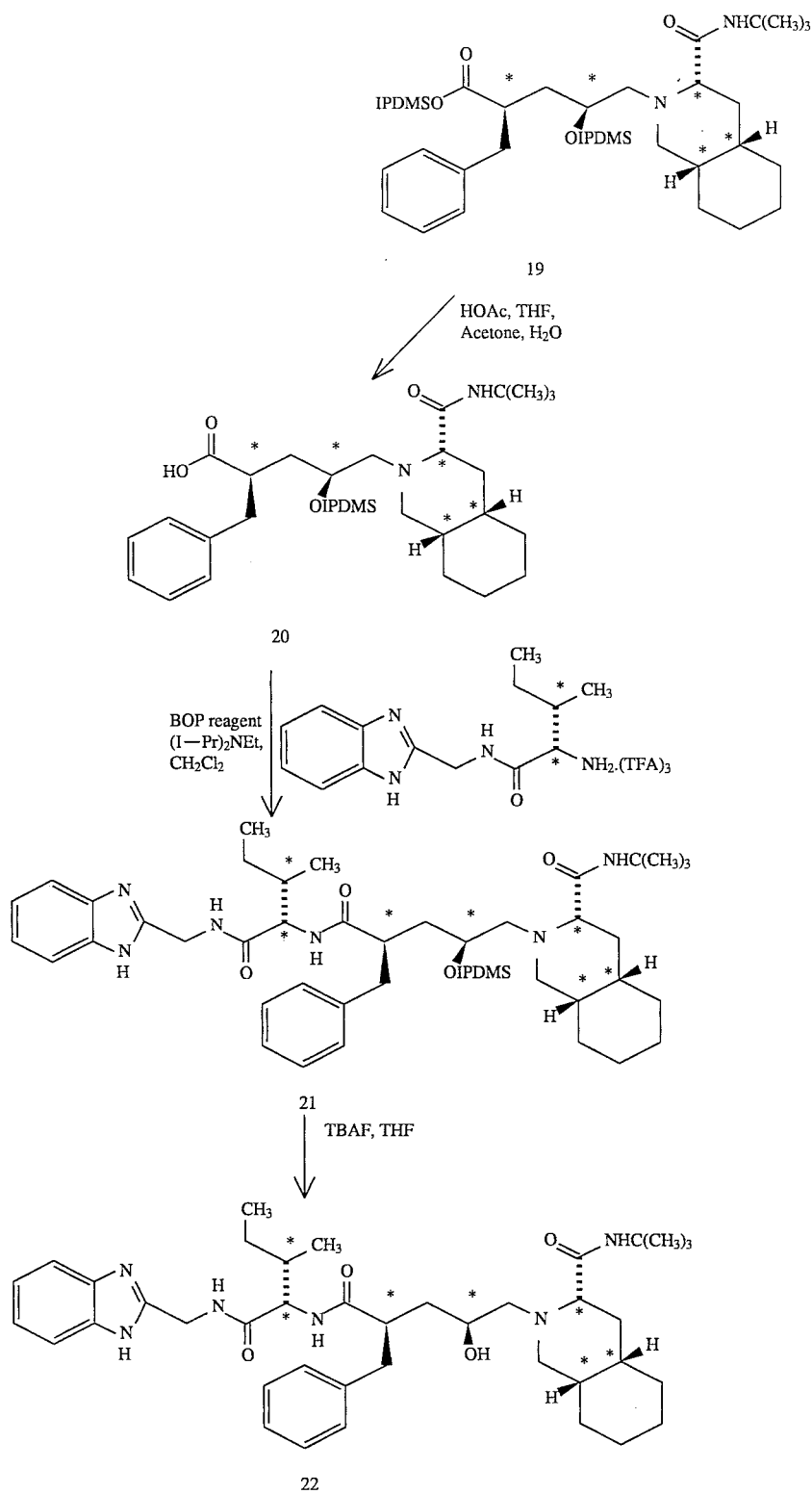

Scheme 6

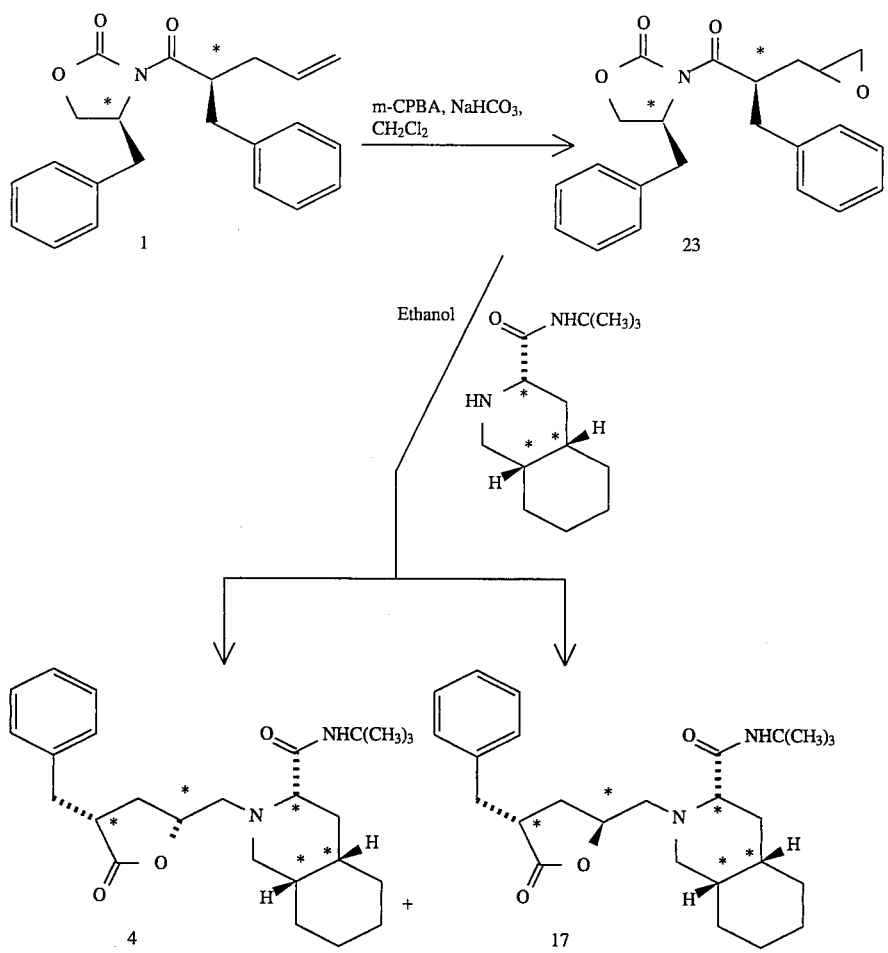

The synthesis of (S)-alpha-2-propenylbenzenepropanoic acid, 2, is described in Scheme 1. (S)-2-oxo-3-(1-oxo-3-phenylpropyl)-4-(phenylmethyl)-2-oxazolidinone is deprotonated with sodium bis(trimethylsilyl)amide (NaHMDS) in tetrahydrofuran at −78° C. It is contemplated that other deprotonating agents known to those skilled in the art may also be employed. The deprotonated compound is then alkylated with ally iodide to provide compound 1. It will be appreciated by those skilled in the art that substituted allyl electrophiles may be employed in the place of allyl iodide. The oxazolidinone portion of 1 is removed by hydrolysis with lithium hydroxide, hydrogen peroxide in aqueous tetrahydrofuran to give acid 2. It is contemplated that other hydrolysing agents known to those skilled in the art may also be employed.

The synthesis of [3S-[2[alphaS*(1R*,2R*), gammaS*(orR*)],3alpha,4abeta,8abeta]]-N-[1[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide, 9, is described in Schemes 2, 3, 4 and 5.

In Scheme 2, acid 2 is subjected to iodolactonization conditions, such as treatment with iodine, potassium iodide and potassium bicarbonate in aqueous tetrahydrofuran to provide iodolactone, 3, which is a 1:4 mixture of isomers (3A-trans:3B-cis). The isomers are purified by known purification techniques including, but not limited to, chromatography. The purified major isomer of this reaction, 3B, is treated with [3S-(3alpha,4beta,8abeta)]-N-(1,1-dimethylethyl)-decahydro-3-isoquinolinecarboxamide, product of Reference Example 4, and N,N-diisopropylethylamine in N,N-dimethylformamide to give lactone, 4. Lactone, 4, is hydrolyzed to compound 5, by reaction with sodium hydroxide in water. It is contemplated that other hydrolysing agents known to those skilled in the art may also be employed. Compound 5, serves as a branch point for Schemes 3 and 4.

The alcohol and carboxylic acid functionalities of compound 5, are protected with suitable protecting agents via reaction with chloroisopropyldimethylsilane (IPDMSCl), triethylamine (NEt₃), and N,N-(dimethylamino)pyridine (DMAP) in methylene chloride to give compound 6. It is contemplated that other suitable carboxylic acid and alcohol protecting agents known to those skilled in the art may also be employed. The acid functionality of compound 6 is selectively deprotected via hydrolysis of the silyl ester by reaction with acetic acid in water, tetrahydrofuran and acetone, to obtain acid, 7. Acid, 7, is coupled to [S-(R*,R*)]-2-amino-N-(1H-benzimidazol-2-ylmethyl)-3-methylpentanamide tris(trifluoroacetate), product of Reference Example 6, by reaction with benzotriazol-1-yloxytris(dimethylamino)phosphonium hexafluorophosphate (BOP) and N,N-diisopropylethylamine in methylene chloride to give compound 8.

The alcohol functionality of compound 8 is deprotected by cleavage of the silyl ether by reaction with tetrabutylammonium fluoride (TBAF) in tetrahydrofuran or by reaction with acetic acid (HOAc) in water to give compound 9.

In Scheme 3, the carboxylic acid and alcohol functionalities of compound 5, are protected with suitable protecting agents via reaction with triphenylsilyl chloride (TPSCl), triethylamine and N,N-(dimethylamino)pyridine in methylene chloride to give compound 10. Selective deprotection of the acid functionality of compound 10is by hydrolysis which occurs by reaction with acetic acid in tetrahydrofuran, acetone and water to give acid, 11. It is contemplated that other hydrolysing agents known to those skilled in the art may also be employed.

Compound, 11, is coupled with [S-(R*,R*)]-2-amino-N-(1H-benzimidazol-2-ylmethyl)-3-methylpentanamide tris-(trifluoroacetate), product of Reference Example 6, by reaction with benzotriazol-1-yloxytris(dimethylamino)phosphonium hexafluorophosphate (BOP) and N,N-diisopropylethylamine in methylene chloride to give compound 12. The alcohol functionality of compound 12 is deprotected by cleavage of the silyl ether by reaction with tetrabutylammonium fluoride in tetrahydrofuran solution to give compound 9. It is contemplated that other reagents known to those skilled in the art may be utilized for such deprotection.

In Scheme 4, the carboxylic acid and alcohol functionalities of compound 5, are protected with suitable protection agents for example via reaction with tert-butyldimethylsilyl chloride (TBDMSCl), imidazole and N,N-dimethylformamide to give compound 13, which is not isolated. The crude reaction mixture is treated with methyl alcohol to deprotect the acid functionality and provide after isolation acid 14.

Acid, 14, is coupled to [S-(R*,R*)]-2-amino-N-(1H-benzimidazol-2-ylmethyl)-3-methylpentanamide tris(trifluoroacetate), product of Reference Example 6, by reaction with benzotriazol-1-yloxytris(dimethylamino)phosphonium hexafluorophosphate (BOP) and N,N-diisopropylethylamine in methylene chloride to give compound 15. The alcohol functionality of compound 15 is deprotected by cleaving the silyl ether by reaction with tetrabutylammonium fluoride in tetrahydrofuran solution or by reaction with acetic acid in water to give compound 9.

In Scheme 5, acid 2 is reacted with dimethylamine, N,N-diisopropylamine, benzotriazol-1-yloxytris(dimethylamino)phosphonium hexafluorophosphate (BOP) and 1-hydroxybenzotriazole (HOBT) in methylene chloride to give amide 16. It will be appreciated by those skilled in the art that other dialkylamines may be employed in place of dimethylamine to produce corresponding dialkylamides. Reaction of amide 16 under iodolactonization conditions with iodine in wet dimethoxyethane provides iodolactone, 3, as a 17:1 mixture of isomers in this reaction (3A-trans:3B-cis). The isomers are purified by known purification techniques, including, but not limited to, chromatography. The purified major iodolactone, 3A, is reacted with [3S-(3alpha,4abeta,8abeta)]-N-(1,1-dimethylethyl)-decahydro-3-isoquinolinecarboxamide, product of Reference Example 4, in the presence of N,N-diisopropylethylamine in N,N-dimethylformamide to give lactone, 17, which is hydrolyzed to hydroxyacid 18 by reaction with aqueous sodium hydroxide.

The carboxylic acid and alcohol functionalities of Compound 18 are protected with suitable protecting agents for example via reaction with chloroisopropyldimethylsilane (IPDMSCl), triethylamine, and N,N-(dimethylamino)pyridine (DMAP), in methylene chloride to give compound 19. It will be appreciated by those skilled in the art that other suitable carboxylic acid and alcohol protecting agents may also be employed. The carboxylic acid functionality of compound 19 is selectively deprotected to give compound 20 by reaction with acetic acid tetrahydrofuran, acetone and water. It is contemplated that other selective deprotecting agents known to those skilled in the art may also be employed. Compound 20, is coupled to [S-(R*,R*)]-2-amino-N-(1H-benzimidazol-2-ylmethyl)-3-methylpentanamide tris(trifluoroacetate), product of Reference Example 6, by reaction with benzotriazol-1yloxytris(dimethylamino) phosphonium hexafluorophosphate (BOP) and N,N-diisopropylethylamine in methylene chloride to give compound 21. The alcohol functionality of compound 21 is deprotected by reaction with tetrabutylammonium fluoride in tetrahydrofuran or hydrolysis with acetic acid in water to give compound 22.

In Scheme 6,-oxazolidinone, 1 is epoxidized via reaction with 3-chloroperoxybenzoic acid (m-CPBA), sodium bicarbonate, in methylene chloride to give epoxide, 23, as a 1:1 ratio of diastereomers. The mixture of isomers, 23, is coupled with [3S-(3alpha,4abeta,8abeta)]-N-(1,1-dimethylethyl)-decahydro-3-isoquinolinecarboxamide, product of Reference Example 4, via displacement of the epoxide and concomitant lactonization to give compounds 4 and 17 in a 1:1 ratio. The two diastereomers are readily separable from one another by known purification techniques, for example, flash chromatography on silica gel.

Lactone, 4, is transformed into compound 9 as described previously in Schemes 2, 3, and 4.

Lactone, 17, is transformed into compound 22 as described previously in Scheme 5.

The protecting groups used in Schemes 2–6 are:

1. isopropyldimethylsilyl ether and isopropyldimethylsilyl ester, or 2. tert-butyldimethylsilyl ether and tert-butyldimethylsilyl ester, or 3. triphenylsilyl ether and triphenylsilyl ester.

It will be appreciated by those skilled in the art that other carboxylic acid and alcohol protecting groups may similarly be employed.

The following non-limiting examples illustrate the processes of the present invention as well as the preparation of novel intermediates.

EXPERIMENTAL

REFERENCE EXAMPLE 1

(S)-2-Oxo-3-(1-oxo-3-phenylpropyl)-4-(phenylmethyl-2-oxazolidinone

To a −78° C. solution of 25 g (S)-(−)-4-benzyl-2-oxazolidinone in 375 ml of dry tetrahydrofuran is added, dropwise, 57 ml of 2.5M n-butyllithium. The mixture is stirred at −78° C. for 15 minutes, 22 ml of hydrocinnamoyl chloride is added and the solution is warmed to room temperature. The reaction is quenched with water, extracted with ethyl acetate, dried and concentrated in vacuo. The residue is recrystallized with ethyl acetate/hexane to give 39 g of the desired product, mp 92°–93° C.

REFERENCE EXAMPLE 2

[3S-(3-alpha,4abeta,8abeta)]-Octahydro-2(1H),3-isoquinolinedicarboxylic acid 1-(phenylmethyl)ester To a 0° C. solution of 3.0 g of [3S-3alpha,4abeta,8abeta)]-decahydro-3-isoquinolinecarboxylic acid in 75 ml of water is added 3.5 ml of 5M sodium hydroxide. After 15 minutes, 6.15 g of benzyl chloroformate is added. During the addition the pH is maintained at >10 with sodium hydroxide. The reaction mixture is stirred at 0° C. for 2 hours, made acidic (pH 2) with 10% hydrochloric acid and extracted with methylene chloride. The organic layer is washed with saturated sodium chloride, dried, filtered and concentrated in vacuo. The residue is purified twice by chromatography (silica gel; gradient elution 0–20% methyl alcohol/chloroform) to give 2.0 g of the desired product.

REFERENCE EXAMPLE 3

[3S-(3alpha,4abeta,8abeta)]-3-[[(1,1-Dimethylethyl)amino]carbonyl]octahydro-2(1)-isoquinolinecarboxylic acid phenylmethyl ester To a room temperature solution of 0.050 g of product from Reference Example 2 in 2 ml of methylene chloride is added 0.090 g of benzotriazol-1-yloxytris(dimethylamino)phosphonium hexafluorophosphate, hereinafter called BOP, 0.015 g of t-butylamine and 0.159 g of triethylamine. The reaction is stirred at room temperature for 5 hours, poured into a solution of half saturated sodium chloride, and extracted with methylene chloride. The organic layer is washed with saturated sodium chloride, dried, filtered and concentrated in vacuo. The residue is purified by chromatography (silica gel; 20% ethyl acetate/hexane) to give 0.046 g of the desired product as a colorless oil.

REFERENCE EXAMPLE 4

[3S-(3alpha,4abeta,8abeta)-N-(1,1-Dimethylethyl)decahydro-3-isoquinolinecarboxamide To a solution of 0.045 g of product from Reference Example 3 in 1 ml of ethyl alcohol is added 0.010 g of 10% Pd/C and the reaction vessel is fitted with a balloon filled with hydrogen. The reaction is stirred at room temperature for 3 hours, filtered and concentrated in vacuo. The residue is purified by chromatography (silica gel; 10% methyl alcohol/chloroform) to give 0.0175 g of product as a colorless oil.

Alternatively, the title compound may be prepared by a one step process.

To a 0° C. solution of 2.0 g of [3S-3alpha,4abeta,8abeta)]-decahydro-3-isoquinolinecarboxylic acid in 40 ml of methylene chloride is added 39.91 g of t-butylamine, 14.11 g of N,N-diisopropylethylamine (Hunig's base), and 6.28 g of BOP in 20 ml of methylene chloride. The reaction is stirred at 0° C. for 1 hour followed by 3 hours at room temperature. The mixture is poured into saturated sodium chloride and extracted with methylene chloride. The organic layer is washed with saturated sodium chloride, dried, filtered and concentrated in vacuo. The residue is purified by chromatography (silica gel; 10% methyl alcohol/chloroform) to give 3.1 g of the desired product as a tan foam.

REFERENCE EXAMPLE 5

[S-(R*,R*)]-1-[[[(1H-Benzimidazol-2-ylmethyl)amino]carbonyl]-2-methylbutyl]carbamic acid 1,1-dimethylethyl ester To a room temperature solution of 0.505 g N-(tert-butoxycarbonyl)-n-isoleucine in 10 ml of methylene chloride is added, in the following order, 0.50 g of 2-(aminomethyl)benzimidazole dihydrochloride hydrate, 1.07 g of BOP and 0.850 g of triethylamine. The reaction is stirred at room temperature for 2 hours, diluted with methylene chloride, and washed with saturated sodium chloride. The organic layer is dried, filtered, and concentrated in vacuo. Purification by chromatography (silica gel; 70% ethyl acetate/hexane) gives 0.669 g of the desired product.

REFERENCE EXAMPLE 6

[S-(R*,R*)]-2-Amino-N-(1H-benimidazol-2-ylmethyl)-3-methylpentanamide tris(trifluoroacetate)

To 0.588 g of product from Reference Example 5 in 6 ml of methylene chloride is added 1.3 ml of trifluoroacetic acid (TFA). The reaction is heated at 80°–90° C. for 4½ hours and concentrated in vacuo to give the desired product.

EXAMPLE 1

[S-(R*,R*)]-3-[1-Oxo-2-(phenylmethyl)-4-pentenyl]-4-(phenylmethyl)-2-oxazolidinone To a –78° C. solution of 339 ml of 1M sodium bis(trimethylsilyl)amine in 300 ml of tetrahydrofuran is added, dropwise over 30 minutes, 100.0 g of (S)-2-oxo-3-(1-oxo-3-phenylpropyl)-4-(phenylmethyl)-2-oxazolidinone, product from Reference Example 1, in 600 ml of tetrahydrofuran. The mixture is stirred at –78° C. for 15 minutes followed by the addition, over 5 minutes, of 108.6 g of allyl iodide in 300 ml of tetrahydrofuran. The reaction is stirred at –78° C. for 1.75 hours, poured into 1.2 L of saturated ammonium chloride and extracted with methylene chloride. The organic layer is washed with saturated sodium chloride, dried and concentrated in vacuo. The residue is purified by chromatography (Silica gel: 15–50% ethyl acetate/hexane) to give 98.3 g (87%) of the desired product as a pale yellow solid.

$[\alpha]_D^{25}$=+121 (c=1.1, CHCl$_3$). Calcd for C$_{22}$H$_{23}$NO$_3$: C=75.62; H=6.63; N=4.01 Found C=75.51; H=6.70; N=4.02

EXAMPLE 2

(S)-alpha-2-Propenyl-benzenepropanoic acid

To a 0° C. solution of 45.0 g of product from Example 1 in 637 ml of tetrahydrofuran and 112 ml of water is added 59 ml of 30% hydrogen peroxide and 8.65 g of lithium hydroxide in 100 ml of water. The reaction is stirred for 3 hours at 0° C. A solution of 58 g of sodium sulfite in 200 ml of water is added to the reaction, stirring is continued for 5 minutes and the mixture is concentrated in vacuo. The residue is extracted with water and methylene chloride. The aqueous layer is cooled to 0° C., made acidic to pH 3 with concentrated hydrochloric acid and extracted with methylene chloride. The methylene chloride layer is washed with saturated sodium chloride, dried, and concentrated in vacuo to give 23.26 g (95%) of the desired product as a pale yellow oil.

$[\alpha]_D^{25}$=+23 (c=1.2, CHCl$_3$). Calcd for C$_{12}$H$_{14}$O$_2$: C=75.76; H=7.42 Found C=75.56; H=7.18

EXAMPLE 3

(3R-cis)-Dihydro-5-(iodomethyl)-3-(phenylmethyl)-2-(3H)-furan-2-one (Isomer B)

(3R-trans)-Dihydro-5-iodomethyl-3-(phenylmethyl)-2(3H)-furan-2-one (Isomer A))

To a room temperature solution of 5.19 g of product from Example 2 in 268 ml of tetrahydrofuran and 132 ml of water is added 13.66 g of potassium hydrogen carbonate, 83.09 g of iodine, and 36.23 g of potassium iodide. The reaction mixture is maintained at room temperature, protected from light, for 5 hours followed by dilution with 1 L of ethyl acetate. The organic layer is washed with saturated sodium bicarbonate, 10% aqueous sodium thiosulfate, dried and concentrated in vacuo. The residue is purified by chromatography (silica gel: 10% ethyl acetate/hexane) to give 2.13 g (25%) of the minor product (Isomer A) and 4.36 g (51%) of the major product (Isomer B). Ratio of isomer A:B is 1:2
Isomer A:
$^1$H NMR(CDCl$_3$):δ 7.38–7.20(m,5H); 4.35–4.28(m,1H); 3.39–3.02(m,4H); 2.85–2.75(m,1H); 2.24–2.06(m,2H).
Isomer B:
$^1$H NMR(CDCl$_3$):δ 7.35–7.27(m,5H); 4.35–4.25(m,1H); 3.40–2.92(m,4H); 2.81–2.75(m,1H); 2.55–2.45(m,1H); 1.75–1.55 (m,1H).

EXAMPLE 4

[3S-[2(2S*,4S*),3alpha,4abeta,8abeta[[-N-(1,1-Dimethylethyl)octahydro-2-[[tetrahydro-5-oxo-4-(phenylmethyl)-2-furanyl]methyl]-3-isoquinolinecarboxamide To a solution of 0.40 g of Isomer B from Example 3 in 10 ml of N,N-dimethylformamide and 0.332 g of [3S-(3alpha, 4abeta,8abeta)]-N-(1,1-dimethylethyl)-decahydro-3-isoquinolinecarboxamide, product from Reference Example 4, is added 242 microliter of N, N-diisopropylethylamine, herinafter called Hunig's base. The reaction mixture is heated at 95° C. for 20 hours, cooled and diluted with saturated aqueous sodium bicarbonate. The aqueous layer is extracted with ethyl acetate, dried and concentrated in vacuo. The residue is purified by chromatography (silica gel: 20–27% ethyl acetate/hexane) to give 0.308 g of the desired product as a colorless foam.
$^1$H NMR(CDCl$_3$):δ 7.30–7.15(m,6H); 6.65(s,1H); 4.52–4.47(m,1H); 3.25–3.20(m,1H); 2.95–2.72(m,3H); 2.60–2.49 (m,2H); 2.30–2.14 (m,4H); 1.83–1.15 (m,11H); 1.31(s,9H).

EXAMPLE 5

[3S-[2[S*(S*)],3alpha,4abeta,8abeta]]-3-[[(1,1-Dimethylethyl)amino]carbonyl]octahydro-gamma-hydroxy-alpha-(phenylmethyl)-2(1H)-isoquinolinepentanoic acid To a solution of 0.370 g of product from Example 4 dissolved in 4 ml of methyl alcohol is added 1.08 ml of 1M sodium hydroxide in water. The mixture is stirred at room temperature for 3.25 hours, diluted with ethyl acetate and the aqueous phase is neutralized to pH 7 with 10% aqueous hydrochloric acid. The separated aqueous layer is extracted with ethyl acetate and the organic layers are combined. The organic layer is washed with saturated sodium chloride, dried and concentrated in vacuo to give 0.39 g of the desired product which is used directly in the next reaction.

EXAMPLE 6

[3S-[2[S*(S*)],3alpha,4abeta,8abeta]]-3-[[(1,1-Dimethylethyl)amino]carbonyl]-gamma-[[dimethyl(1-methylethyl)silyl]oxy]octahydro-alpha-(phenylmethyl)-2(1H)-isoquinolinepentanoic acid dimethyl(1-methylethyl)silyl ester To a solution of 0.208 g of product from Example 5 in 5 ml of methylene chloride is added 0.003 g of 4-(dimethylamino)pyridine, 326 microliter of triethylamine, and 221 microliter of chlorodimethylisopropylsilane. The reaction is stirred for 17 hours, diluted with saturated sodium chloride and saturated aqueous sodium bicarbonate, and extracted with methylene chloride. The combined organic layers are washed with saturated sodium chloride, dried and concentrated to give 0.34 g of the desired product which is used directly in the next reaction.

EXAMPLE 7

[3S-[2[S*(S*)],3alpha,4abeta,8abeta]]-3-[[(1,1-Dimethylethyl)amino]carbonyl]-gamma-[[dimethyl(1-methylethyl)silyl]oxy]octahydro-alpha-(phenylmethyl)-2(1H)-isoquinolinepentanoic acid A 1:1 solution of water and acetone is prepared. Glacial acetic acid is added to adjust the pH to 5.
To a 0° C. solution of 0.30 g of product from Example 6 in 3 ml of tetrahydrofuran is added 0.75 ml of the acetone/water/acetic acid solution prepared above. The reaction is stirred at 0° C. for 30 minutes followed by stirring at room temperature for 1.25 hours. The mixture is concentrated in vacuo, toluene is added and the mixture is reconcentrated to remove the residual water and acetic acid. The product, 0.30 g, is isolated and used directly in the next reaction.

EXAMPLE 8

[3S-[2[2S*,4S*(1R*,2R*)],3alpha,4abeta,8abeta]]-2-[5[[1-[[(1H-benzimidazol-2-ylmethyl)amino]carbonyl-2-methylbutyl]amino]-2-[[dimethyl(1-methylethyl)silyl]oxy]-5-oxo-4-(phenylmethyl)pentyl]-N-(1,1-dimethylethyl)decahydro-3-isoquinolinecarboxamide To a solution of 0.25 g of product from Example 7 in 7 ml of methylene chloride is added 799 microliter of Hunig's base, 0.553 g of [S-(R*,R*)]-2-amino-N-(1H-benzimidazol-2-ylmethyl)-3-methylpentanamide tris(trifluroroacetate), product from Reference Example 6, and 0.405 g of BOP. The reaction mixture is stirred at room temperature for 17 hours followed by dilution with half saturated sodium chloride and extraction with methylene chloride. The organic layers are washed with saturated sodium chloride, dried and concentrated in vacuo. The residue is purified by chromatography (silica gel: 5% methyl alcohol/chloroform) to give 0.282 g of the desired product as a colorless foam.
$^1$H NMR(CDCl$_3$):δ 10.51(s,1H); 7.75(br s,1H); 7.47(br s,1H); 7.30–7.18(m,7H); 6.97(br s,2H); 6.35(s,1H); 5.45(br s,1H); 4.79–4.70(m,1H); 4.19(t,1H); 4.10–4.04(m,1H); 3.92–3.85(m,1H); 2.90–2.30(m,4H); 2.20–1.15(m,21H); 1.44(s,9H); 1.07–0.8(m,12H); 0.15 ( s,3H); 0.07 (s,3H). MS(FAB): m/z 787 (M$^+$+H).

EXAMPLE 9

[3S-[2(alphaS*(1R*,2R*),gammaR*),3alpha,4abeta,8abeta]]-N-[1[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide To a 0.025 g solution of product from Example 8 in 1 ml of tetrahydrofuran is added 0.32 ml of 1M tetrabutylammonium fluoride, hereinafter called TBAF, in tetrahydrofuran. The reaction is stirred for 30 minutes, diluted with water and the pH is adjusted to 5, and extracted with chloroform. The organic layers are washed with saturated sodium chloride, dried and concentrated in vacuo. The residue is purified by chromatography (silica gel: 10% methyl alcohol/chloroform) to give 0.0181 g of the desired product.
MS (FAB):m/z 687 (M$^+$+H) . $^1$H NMR(CDCl$_3$):δ 7.57(brs,2H); 7.34(brs,1H); 7.24–7.18(m,2H); 7.14–7.00(m, 6H); 6.91(brs,1H); 6.18(s,1H); 4.68–4.42(m,2H); 4.23(t, 1H); 3.80–3.69(m,2H); 2.94–1.00(24H); 1.32(s,9H); 0.89–0.77 (m,6H).

EXAMPLE 10

[3S-[2[S*(S*)],3alpha,4abeta,8abeta]]-3-[[(1,1-Dimethylethyl)amino]carbonyl]octahydro-alpha-(phenylmethyl)-gamma-[(triphenylsilyl)oxy]-2(1H)-isoquinolinepentanoic acid triphenylsilyl ester The title compound is prepared by the procedure of Example 6 using 0.193 g of product of Example 5 in 5 ml of methylene chloride, 303 microliter of triethylamine, 0.0027 g of DMAP and 0.384 g of triphenylsilyl chloride to give 0.534 g of the desired product which is used directly in the next reaction.

EXAMPLE 11

[3S-[2[S*(S*)],3alpha,4abeta,8abeta]]-3[[(1,1-Dimethylethyl)amino]carbonyl]octahydro-alpha-(phenylmethyl)-gamma-[(triphenylsilyl)oxy]-2(1H)-isoquinolinepentanoic acid The title compound is prepared by the procedure of Example 7 using 0.42 g of product from Example 10 in 2.5 ml of tetrahydrofuran, 1.0 ml of acetone/water/acetic acid solution to give 0.233 g of the desired product which is used directly in the next reaction.

EXAMPLE 12

[3S-[2[2S*,4S*(1R*,2R*)],3alpha,4abeta,8abeta]]-2-[5-[[1-[[(1H-benzimidazol-2-ylmethyl)amino]carbonyl]-2-methylbutyl]amino]-5-oxo-4-(phenylmethyl)-2-[(triphenylsilyl)oxy]pentyl]-3-isoquinolinecarboxamide The title compound is prepared by the procedure of Example 8 using 0.305 g of product from Example 11 in 6 ml of methylene chloride, 756 microliter of N,N-diisoprpylethylamine, 0.523 g of [S-(R*,R*)]-2-amino-N-(1H-benzimidazol-2-ylmethyl)-3-methylpentanamide tris(trifluroroacetate), product of Reference Example 6, and 0.384 g of BOP to give 0.242 g of the desired product after chromatography.

MS(FAB): m/z 945 (M$^+$+H).

EXAMPLE 13

[3S-[2(alphaS*(1R*,2R*),gammaR*],3alpha,4abeta,8abeta]]-N-[1[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2-isoquinolinepentanamide The title compound is prepared by the procedure of Example 9 using 0.032 g of product from Example 12 in 1 ml of tetrahydrofuran, 0.34 ml of 1M TBAF solution to give 0.028 g of the desired product.

MS (FAB):m/z 687 (M$^+$+H). $^1$H NMR(CDCl$_3$):δ 7.57(brs,2H); 7.34(brs,1H); 7.24–7.18(m,2H); 7.14–7.00(m,6H); 6.91(brs,1H); 6.18(s,1H); 4.68–4.42(m,2H); 4.23(t,1H); 3.80–3.69(m,2H); 2.94–1.00(24H); 1.32(s,9H); 0.89–0.77 (m, 6H).

EXAMPLE 14

[3S-[2[S*(S*)],3alpha,4abeta,8abeta]]-3-[[(1,1-dimethylethyl)amino]carbonyl]-gamma-[[(1,1-dimethylethyl)dimethylsilyl]oxy]octahydro-alpha-(phenylmethyl)-2(1H)-isoquinolinepentanoic acid (1,1-dimethylethyl)dimethylsilyl ester To 0.222 g of product from Example 5 in 3 ml of N,N-dimethylformamide is added 0.136 g of imidazole and 0.263 g of t-butyldimethylsilyl chloride. The reaction is stirred at room temperature for 16 hours and concentrated in vacuo and used in the following reaction.

EXAMPLE 15

[3S-[2[S*(S*)],3alpha,4abeta,8abeta]]-3-[[(1,1-dimethylethyl)amino]carbonyl]-gamma-[[(1,1-dimethylethyl)dimethylsilyl]oxy]octahydro-alpha-(phenylmethyl)-2(1H)-isoquinolinepentanoic acid The crude reaction mixture from Example 14 is stirred with 10 ml of methyl alcohol at room temperature for 4.5 hours. The mixture is concentrated in vacuo, diluted with water, and extracted with ethyl acetate. The organic layer is washed with saturated sodium chloride, dried and concentrated in vacuo. The residue is used in the following reaction.

MS(FAB): m/z 559 (M$^+$+H).

EXAMPLE 16

[3S-[2[gammaS*,alphaS*(1R*,2R*),3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]-gamma-[[(1,1-dimethylethyl)dimethylsilyl]oxy]-3,4,4a,5,6,7,8,8a-octahydro-alpha-(phenylmethyl)-2(1H)-isoquinolinepentanamide The title compound is prepared by the procedure of Example 8 using 0.278 g of product from Example 15, 0.599 g of [S-(R*,R*)]-2-amino-N-(1H-benzimidazol-2-ylmethyl)-3-methylpentanamide tris(trifluoroacetate), product of Reference Example 6, 0.440 g of BOP, 0.643 g of Hunig's base and 7 ml of methylene chloride to give 0.294 g of the desired product.

MS(FAB): m/z 801 (M$^+$+H).

EXAMPLE 17

[3S-[2[alphaS*(1R*,2R*),gammaR*],3alpha,4abeta,8abeta]]-N-[1[[(1H-Benzimidazol-2ylmethyl)amino]carbonyl]-2-methylbutyl]-3[[(1,1-dimethylethyl)amino]carbonyl]decahydro-gamma-hydroxy-alpha-(phenylmethyl)-2-isoquinolinepentanamide The title compound is prepared by the procedure of Example 9 using 0.050 g of product from Example 16, 1.24 ml of 1M TBAF and 2 ml of tetrahydrofuran to give 0.050 g of the desired product.

MS(FAB):m/z 687 (M$^+$+H).

$^1$H NMR (CDCl$_3$):δ 7.57 (brs, 2H); 7.34(brs,1H); 7.24–7.18(m,2H); 7.14–7.00(m,6H); 6.91(brs,1H); 6.18(s,1H); 4.68–4.42(m,2H); 4.23(t,1H); 3.80–3.69(m,2H); 2.94–1.00(24H); 1.32(s,9H); 0.89–0.77 (m, 6H).

EXAMPLE 18

N,N-Dimethyl-alpha-2-propenylbenzenepropanamide

To a 0° C. solution of 22.95 g of product from Example 2 in 550 ml of methylene chloride is added 9.68 g of dimethylamine hydrochloride and 58.69 g of BOP. Let stir a few minutes and then add 1.0 g of 1-hydroxybenzotriazole hydrate (HOBT) and 155.9 g of Hunig's base. The reaction is stirred in the cold for 7 hours then allowed to warm to room temperature overnight. The reaction is diluted with half saturated sodium chloride and extracted with methylene chloride. The organic layer is washed with saturated sodium chloride, dried and concentrated in vacuo. The residue is purified by chromatography (silica gel: 7–30% ethyl acetate/hexane) to give 24.68 g of the desired product.

MS(CI):m/z 217(M$^+$). $[\alpha]_D^{25}$=+38 (C=1.1, CHCl$_3$).

EXAMPLE 19

(3R-trans)-Dihydro-5-iodomethyl-3-(phenylmethyl)-2(3H)-furan-2-one (Isomer A)

(3R-cis)-Dihydro-5-(iodomethyl)-3-(phenylmethyl)-2(3H)-furan-2-one (Isomer B)

To 24 g of product from Example 18 is added 200 ml of dimethoxyethane and 200 ml of water. The solution is stirred and cooled at −20° C., in the dark, for 30 minutes. Iodine, 33.64 g, is added and the stirring at −20° C. continued for 5 hours followed by stirring at room temperature for 3 days. The reaction is diluted with 1 L of ethyl acetate, washed with 1 L of 10% sodium bicarbonate and is extracted with ethyl acetate. The organic layer is washed with sodium bicarbonate, dried, and concentrated in vacuo. The residue is purified by repeated chromatography (silica gel: 5–10% ethyl acetate/hexane) to give 27.3 g of the isomer product (A) and 1.6 g of isomer product (B). Ratio of isomers (A:B) from this reaction is 17:1. The isomers were also made in Example 3 and the ratio (A:B) is 1:2.

EXAMPLE 20

[3S-[2(2R*,4S*),3alpha,4abeta,8abeta]]-N-(1,1-Dimethylethyl)decahydro-2-[[tetrahydro-5-oxo-4-(phenylmethyl)-2-furanyl]methyl]-3-isoquinolinecarboxamide The title compound is prepared by the procedure of Example 4 using 27 g of product from Example 19, 20.36 of [3S-(3alpha,4abeta,8abeta)]-N-(1,1-dimethylethyl)decahydro-3-isoquinolinecarboxamide, product of Reference Example 4, 600 ml of N,N-dimethylformamide and 16.36 ml of Hunigs base to give 10.3 g of the desired product after purification by chromatography.

MS(FAB):m/z 427 (M$^+$+H). $[\alpha]_D^{25}$=−69 (c=1.1, CHCl$_3$).

EXAMPLE 21

[3S-[2R*(S*)],3alpha,4abeta,8abeta]]-3-[[(1,1-Dimethylethyl)amino]carbonyl]octahydro-gamma-hydroxy-alpha-(phenylmethyl)-2(1H)-isoquinolinepentanoic acid The title compound is prepared by the procedure of Example 5 using 0.25 g of product from Example 20, 0.73 ml of sodium hydroxide in water and 2.5 ml of methyl alcohol to give 0.270 g of the product which is used directly in the next reaction.

EXAMPLE 22

[3S-[2[R*(S*)],3alpha,4abeta,8abeta]]-3-[[(1,1-Dimethylethyl)amino]carbonyl]-gamma-[[dimethyl(1-methylethyl)silyl]oxy]octahydro-alpha-(phenylmethyl)-2(1H)-isoquinolinepentanoic acid dimethyl(1-methylethyl)silyl ester The title compound is prepared by the procedure of Example 6 using 10.0 g of product from Example 21, 261 ml of methylene chloride, 0.143 g of DMAP, 16.33 ml of triethylamine and 11.07 ml of chlorodimethylisopropylsilane to give the desired product which is used directly in the next reaction.

MS(FAB):m/z 545 (M$^+$+H-C$_5$H$_{13}$Si). $[\alpha]_D^{25}$=−31+1 (c=1.2)

EXAMPLE 23

[3S-[2[R*(S*)],3alpha,4abeta,8abeta]]-3-[[(1,1-Dimethylethyl)amino]carbonyl]-gamma-[[dimethyl(1-methylethyl)silyl]oxy]octahydro-alpha-(phenylmethyl)-2(1H)-isoquinolinepentanoic acid The title compound is prepared by the procedure of Example 7 using 15.12 g of product from Example 22, 152 ml of tetrahydrofuran and 39 ml of acetone/water/acetic acid (pH=4) to give the desired product which is used directly in the next reaction.

MS(FAB):m/z 545 (M$^+$+H).

EXAMPLE 24

[3S-[2[2S*,4R*(1R*,2R*)],3alpha,4abeta,8abeta]]-2-[5-[[1-[[(1H-Benzimidazol-2-ylmethyl)amino]carbonyl]-2-methylbutyl]amino]-2-[[dimethyl(1-methylethyl)silyl]oxy]-5-oxo-4-(phenylmethyl)pentyl]-N-(1,1dimethylethyl)decahydro-3-isoquinolinecarboxamide The title compound is prepared by the procedure of Example 8 using 12.77 g of product from Example 23, 365 ml of methylene chloride, 28.24 g of [S-(R*,R*)]-2-amino-N-(1H-benzimidazol-2-ylmethyl)-3-methylpentanamide tris(trifluroroacetate), (prepared by the procedure described in Serial No. 991,876, Example 12), 40.83 ml of Hunigs base and 2.71 g of BOP to give 5.4 g of the desired product.

MS(FAB):m/z 787 (M$^+$+H).

EXAMPLE 25

[3S-[2[alphaS*(1R*,2R*),gammaS*]3alpha,4abeta,8abeta]]-N-[1-[[(1H-Benzimidazol-2-ylmethyl)amino]carbonyl]-2-methylbutyl]-3-[[(1,1-dimethylethyl)amino]carbonyl]decahydro-gamma-hydroxy-alpha-(phenylmethyl)-2isoquinolinepentanamide The title compound is prepared by the procedure of Example 9 using 5.3 g of product from Example 24, 200 ml of tetrahydrofuran, and 67.33 g of TBAF to give 2.53 g of the desired product.

$^1$H NMR(CDCl$_3$)δ 7.58(brs,2H); 7.30–7.21(m,2H); 7.15–7.00(m,6H); 6.74(brs,1H); 6.12(brs,1H); 4.72–4.17 (m, 3H); 3.84–3.68 (m, 1H); 3.25–3.11 (m, 1H); 2.91–1.0(m, 24H); 1.35(s,9H); 0.92–0.75(m,6H). MS(FAB):m/z 687 (M$^+$+H).

EXAMPLE 26

[2R-[2R*(4S*),2(R*)]]-3-[2-(Oxiranylmethyl)-1-oxo-3-phenylpropyl]-4-(phenylmethyl)-2-oxazolidinone and

[2R-[2R*(4S*),2(S*)]]-3-[2-(Oxiranylmethyl)-1-oxo-3-phenylpropyl]-4-(phenylmethyl)-2-oxazolidinone To a 0° C. solution of 1.0 g of product from Example 1, 25 ml of methylene chloride, and 0.721 g of sodium bicarbonate is added 1.41 g of m-chloroperbenzoic acid. The reaction is stirred at 0° C. for 3 hours followed by room temperature stirring for 67 hours. The mixture is diluted with methylene chloride and water and the layers are separated. The organic layer is washed with saturated sodium chloride, dried and concentrated in vacuo. The residue is purified by chromatography (silica gel: 20% ethyl acetate/hexane) to give 0.81 g of the desired product.

MS(EI):m/z 365 (M$^+$). [$\alpha$]$_D^{25}$=+101±1 (CHCl$_3$).

EXAMPLE 27

[3S-[2[2S*,4S*),3alpha,4abeta,8abeta]]-N-(1,1-Dimethylethyl)decahydro-2-[[tetrahydro-5-oxo-4-(phenylmethyl)-2-furanyl]methyl]-3-isoquinolinecarboxamide and

[3S-[2[2R*,4S*),3alpha,4abeta,8abeta]]-N-(1,1-Dimethylethyl)decahydro-2-[[tetrahydro-5-oxo-4-(phenylmethyl)-2-furanyl]methyl]-3-isoquinolinecarboxamide To 1.0 g of product from Example 26 is added 1.53 g of [3S-(3alpha,4abeta,8abeta)]-N-(1,1-dimethylethyl)decahydro-3-isoquinolinecarboxamide, product from Reference Example 4, and 30 ml of ethyl alcohol. The reaction mixture is heated at reflux temperature 48 hours then concentrated in vacuo and stored in the freezer. The residue is purified by chromatography (silica gel: 20–27% ethyl acetate/hexane) to give 0.723 g of a 1:1 mixture of isomers. The mixture is further purified by chromatography to give: [3S-[2(2S*,4S*),3alpha,4abeta,4abeta]]-N-(1,1-dimethylethyl)octahydro-2-[[tetrahydro-5-oxo-4-(phenylmethyl)-2-furanyl]methyl]-3-isoquinolinecarboxamide, identical product as product from Example 4, and [3S-[2(2R*,4S*),3alpha,4abeta,8abeta]]-N-(1,1-dimethylethyl)decahydro-2-[[tetrahydro-5-oxo-4-(phenylmethyl)-2-furanyl]methyl]-3-isoquinolinecarboxamide, identical product as product from Example 20.

What is claimed is:

1. A method of making a compound of formula III:

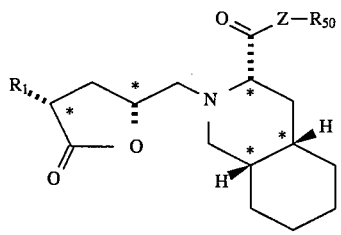

III wherein:

$R_{50}$ is a straight or branched (C$_1$–C$_7$)alkyl;

Z is a single bond, oxygen or NH;

$R_1$ is hydrogen; straight or branched (C$_1$–C$_7$)alkyl; —(CH$_2$)$_n$-cyclic(C$_3$–C$_7$)alkyl, n=0–4; —(CH$_2$)$_n$-phenyl, n=0–4; or —(CH$_2$)$_n$-substituted phenyl, n=0–4, and substituted with F, Cl, Br, I, (C$_1$–C$_4$)alkoxide, straight or branched (C$_1$–C$_6$)alkyl or (C$_3$–C$_6$)cycloalkyl which comprises:

a) deprotonating a compound of the formula:

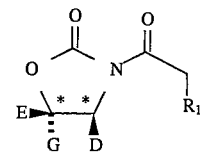

wherein $R_1$ is as defined hereinabove;

D is (C$_1$–C$_7$)alkyl or —(CH$_2$)$_n$-phenyl, n=0–4; and

E and G are the same or different and are hydrogen, (C$_1$–C$_7$)alkyl or —(CH$_2$)$_n$-phenyl, n=0–4; and then alkylating with allyl iodide to obtain a compound of the formula:

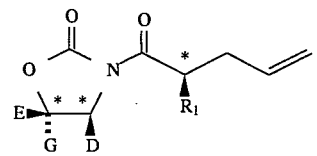

wherein $R_1$, D, E, and G are as defined hereinabove;

b) hydrolyzing the compound obtained from step a to remove the oxazolidinone portion and obtain a compound of the formula:

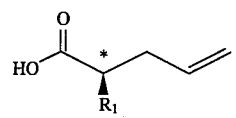

wherein $R_1$ is as defined hereinabove;

c) subjecting the compound obtained from step b to iodolactonization conditions to obtain a mixture of diastereomers, 3R-cis, 3R-trans, of the formula:

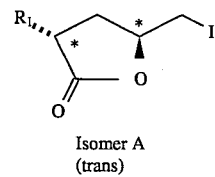 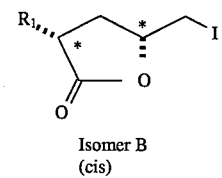

Isomer A (trans)    Isomer B (cis)

wherein $R_1$ is as defined hereinabove and separating the isomers to obtain a purified cis-iodolactone (isomer B); and d) coupling the purified cis-iodolactone (Isomer B) obtained from step c with a compound of formula:

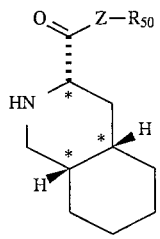

via iodide displacement wherein $R_{50}$ and Z are as defined hereinabove; and obtaining a compound of formula III.

2. The method according to claim 1 further comprising:
 a) hydrolyzing the compound of Formula III to obtain a compound of the formula:

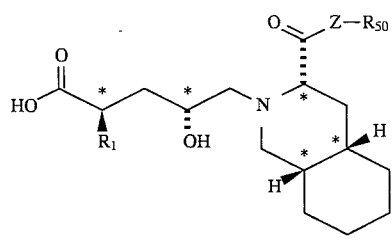

wherein $R_1$, $R_{50}$ and Z are as defined hereinabove;

b) protecting the alcohol and carboxylic acid functionalities of the compound obtained from step a to obtain a compound of the formula:

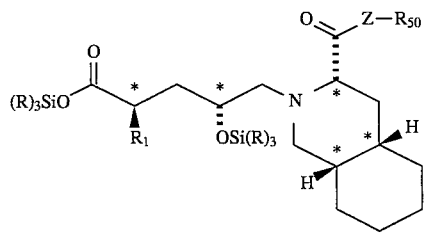

wherein $R_1$, $R_{50}$ and Z are as defined hereinabove and R is a straight or branched $(C_1-C_6)$ alkyl or phenyl;

c) selectively deprotecting the carboxylic acid functionality of the compound obtained from step b to obtain a compound of the formula:

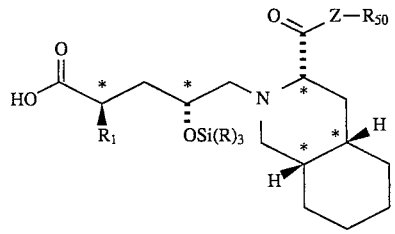

wherein R, $R_1$, $R_{50}$ and Z are as defined hereinabove;

d) reacting the deprotected carboxylic acid functionality of the compound obtained from step c with a compound of the formula:

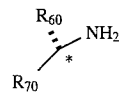

wherein $R_{60}$ is a straight or branched $(C_1-C_7)$alkyl; $-(CH_2)_n$-cyclic $(C_3-C_7)$alkyl, n=0–4; $-(CH_2)_2CONH_2$; $-CH_2CONH_2$; $-CH_2OH$ or $-CH(CH_3OH$; and $R_{70}$ is a moiety of the formula:

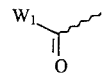

wherein $W_1$ is $-NH(CH_2)_j$-phenyl, j=0–1; $-NH(CH_2)_j$-substituted phenyl, j=0–1, substituted with F, Cl, Br, I, $(C_1-C_4)$alkoxide, straight, branched or cyclic $(C_1-C_6)$alkyl; $-NH(CH_2)_j$-T, j=0–1, wherein T is selected from piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoazolidinyl, morpholinyl, thiazolyl, thiazolidinyl, isothiazolyl, benzofuranyl, benzodioxanonyl, quinuclidinyl, isothiazolidinyl, indolyl, quinolinyl, isoquinolinyl, benzimidazolyl, thiadiazoyl, benzopyranyl, benzothiapyranyl, benzothiazolyl, benzoxaolyl, furyl, tetrahydrofuryl, tetrahydropyranyl, thienyl, benzothienyl, thiamorpholinyl, thiamorpholinyl sulfoxide, thiamorpholinyl sulfone and oxadiazolyl; or $-NH(CH_2)_j$-substituted T, j=0–1, T is as defined hereinabove, substituted with F, Cl, I, Br, $(C_1-C_4)$alkoxide, or straight, branched or cyclic $(C_1-C_6)$alkyl; to obtain a compound of the formula:

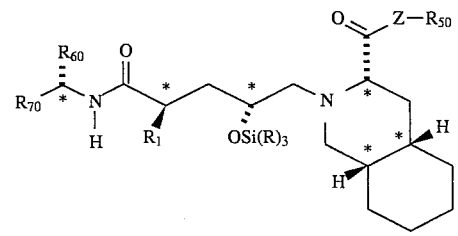

wherein R, $R_1$, $R_{50}$, $R_{60}$, $R_{70}$ and Z are as defined hereinabove; and e) deprotecting the alcohol functionality of the compound obtained from step d to obtain the compound of formula Ib:

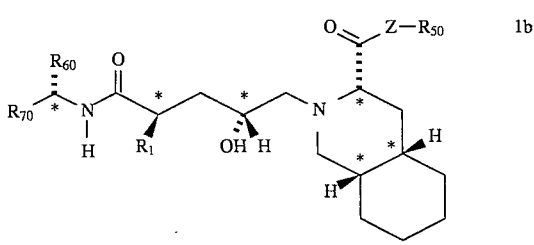

wherein $R_1$, $R_{50}$, $R_{60}$, $R_{70}$ and Z are as defined hereinabove.

* * * * *